United States Patent
Moran et al.

(10) Patent No.: US 9,788,925 B2
(45) Date of Patent: Oct. 17, 2017

(54) TRANSDUCER ACTIVATED TOOL WITH WATER CONDUIT

(71) Applicants: Vicky L Moran, York, PA (US); Kevin Lint, Seven Valleys, PA (US)

(72) Inventors: Vicky L Moran, York, PA (US); Kevin Lint, Seven Valleys, PA (US)

( * ) Notice: Subject to any disclaimer, the term of this patent is extended or adjusted under 35 U.S.C. 154(b) by 0 days.

(21) Appl. No.: 13/850,643

(22) Filed: Mar. 26, 2013

(65) Prior Publication Data
US 2013/0209955 A1 Aug. 15, 2013

Related U.S. Application Data

(63) Continuation of application No. 12/859,366, filed on Aug. 19, 2010, now abandoned.

(60) Provisional application No. 61/274,600, filed on Aug. 19, 2009.

(51) Int. Cl.
A61C 1/07 (2006.01)
A61C 17/20 (2006.01)
A61C 3/03 (2006.01)

(52) U.S. Cl.
CPC .............. *A61C 17/20* (2013.01); *A61C 1/07* (2013.01); *A61C 3/03* (2013.01); *Y10T 29/49567* (2015.01)

(58) Field of Classification Search
CPC ............ A61C 17/0202; A61C 17/0211; A61C 17/0214; A61C 17/0217; A61C 17/036; A61C 17/20; A61C 17/227; A61C 3/00; A61C 15/00
USPC ............... 433/80–82, 86, 141–147, 218–219
See application file for complete search history.

(56) References Cited

U.S. PATENT DOCUMENTS

| | | |
|---|---|---|
| 3,076,904 A | 2/1963 | Kleesattel et al. |
| 3,124,787 A | 3/1964 | Bartik |
| 3,368,280 A | 2/1968 | Friedman et al. |
| 3,375,583 A | 4/1968 | Blank et al. |
| 3,488,851 A | 1/1970 | Haydu |
| 3,522,801 A | 8/1970 | Robinson |
| 3,526,036 A | 9/1970 | Goof |
| 3,589,012 A | 6/1971 | Richmman |
| 3,703,037 A | 11/1972 | Robinson |
| 3,924,335 A | 12/1975 | Balamuth et al. |
| 3,930,173 A | 12/1975 | Banko |
| 4,110,908 A | 9/1978 | Cranston |
| 4,176,454 A | 12/1979 | Hatter et al. |
| RE30,536 E | 3/1981 | Perdreaux, Jr. |

(Continued)

FOREIGN PATENT DOCUMENTS

| | | |
|---|---|---|
| DE | 29810111 U1 | 11/1998 |
| EP | 0217890 B1 | 4/1987 |

(Continued)

*Primary Examiner* — Yogesh Patel
(74) *Attorney, Agent, or Firm* — Leona Levin; Douglas J. Hora; David A. Zdvine

(57) ABSTRACT

A device includes a connecting end and a working end. Device has an internal fluid passageway and a bend area. The fluid passageway has a discharge opening or hole, which opening is positioned or located substantially away from the bend area, such that the discharge opening and upstream portions of the passageway will remain unaffected, substantially unaffected, or selectively affected by any deformation thereof due to the bending procedures employed to make the other portions of the tool, such as those conventionally involved in fabricating the bend area.

16 Claims, 3 Drawing Sheets

(56) References Cited

U.S. PATENT DOCUMENTS

| | | | |
|---|---|---|---|
| 4,283,175 A | 8/1981 | Nash | |
| 4,332,558 A | 6/1982 | Lustig | |
| 4,370,131 A | 1/1983 | Banko | |
| 4,501,558 A | 2/1985 | Maliga | |
| 4,578,033 A * | 3/1986 | Mossle et al. | 433/29 |
| 4,731,019 A | 3/1988 | Martin | |
| 4,787,847 A | 11/1988 | Martin et al. | |
| 4,992,048 A | 2/1991 | Goof | |
| 5,094,617 A | 3/1992 | Carr | |
| 5,125,837 A * | 6/1992 | Warrin | B23Q 1/0036 433/216 |
| 5,125,838 A | 6/1992 | Seigneurin | |
| 5,190,456 A | 3/1993 | Hasegawa | |
| 5,199,456 A * | 4/1993 | Love | F23N 1/005 137/269 |
| 5,236,358 A | 8/1993 | Sieffert | |
| 5,331,597 A | 7/1994 | Tanaka | |
| 5,419,703 A * | 5/1995 | Warrin et al. | 433/216 |
| 5,431,565 A | 7/1995 | Euvrard | |
| 5,567,153 A * | 10/1996 | Foulkes | A61C 3/03 433/119 |
| 5,704,787 A | 1/1998 | Hickok et al. | |
| 5,725,370 A * | 3/1998 | Himeno et al. | 433/86 |
| 5,733,119 A | 3/1998 | Carr | |
| 5,749,727 A * | 5/1998 | Dao | A61C 3/03 433/119 |
| 5,772,434 A | 6/1998 | Winston | |
| 5,775,901 A | 7/1998 | Riso | |
| 5,836,765 A | 11/1998 | Hickok | |
| 5,853,290 A | 12/1998 | Winston | |
| 5,868,570 A | 2/1999 | Hickok et al. | |
| 5,899,693 A | 5/1999 | Himeno et al. | |
| 6,086,369 A | 7/2000 | Sharp et al. | |
| 6,168,069 B1 | 1/2001 | Lorenz | |
| D450,847 S | 11/2001 | Feine | |
| 6,494,714 B1 * | 12/2002 | Copeland | 433/86 |
| 6,722,882 B2 | 4/2004 | Buchanan | |
| 6,726,531 B1 | 4/2004 | Harrel | |
| 6,810,585 B2 | 11/2004 | Hickok | |
| 6,817,862 B2 | 11/2004 | Hickok | |
| 6,872,125 B2 | 3/2005 | Harrel | |
| 7,140,878 B2 | 11/2006 | Hickok | |
| 7,172,420 B2 | 2/2007 | Huguenin et al. | |
| 7,217,128 B2 | 5/2007 | Atkin et al. | |
| 2002/0119419 A1 * | 8/2002 | Suzuki | A61C 1/08 433/118 |
| 2002/0168611 A1 | 11/2002 | Kim | |
| 2003/0157458 A1 * | 8/2003 | Buchanan | 433/166 |
| 2004/0023187 A1 | 2/2004 | Hickok | |
| 2005/0130102 A1 | 6/2005 | Pring | |
| 2005/0136375 A1 | 6/2005 | Sicurelli, Jr. et al. | |
| 2005/0181328 A1 | 8/2005 | Milne | |
| 2005/0244788 A1 | 11/2005 | Feine | |
| 2007/0254262 A1 | 11/2007 | Doussin et al. | |
| 2007/0259307 A1 | 11/2007 | Quan et al. | |
| 2007/0275348 A1 | 11/2007 | Lemon | |
| 2008/0057469 A1 | 3/2008 | Hayman et al. | |
| 2008/0254409 A1 * | 10/2008 | Hwang | A61C 3/03 433/143 |

FOREIGN PATENT DOCUMENTS

| | | |
|---|---|---|
| EP | 0323598 B1 | 7/1989 |
| EP | 0719526 B1 | 7/1996 |
| EP | 0746262 B1 | 12/1996 |
| EP | 1120092 B1 | 8/2001 |
| EP | 1818022 A1 | 8/2007 |
| WO | 1998025536 A1 | 6/1998 |
| WO | 2000057806 A1 | 10/2000 |
| WO | 2003043520 A1 | 5/2003 |
| WO | 2003070121 A1 | 8/2003 |
| WO | 2004082502 A2 | 9/2004 |
| WO | 2005025439 A2 | 3/2005 |
| WO | 2005039395 A2 | 5/2005 |
| WO | 2006034281 A1 | 3/2006 |
| WO | 2007130748 A1 | 11/2007 |

* cited by examiner

TRANSDUCER ACTIVATED TOOL WITH WATER CONDUIT

The present application is a continuation of U.S. patent application Ser. No. 12/859,366 having a filing date of Aug. 19, 2010, now pending, which claims priority to U.S. Provisional Application No. 61/307,920 having a filing date of Feb. 25, 2010, and U.S. Provisional Application No. 61/274,600 having a filing date of Aug. 19, 2009.

TECHNICAL FIELD

Disclosed herein is a transducer activated tool for contacting workpiece surfaces and directing a fluid adjacent to the workpiece. More particularly, the tool described herein relates to an ultrasonically activated tool such as a dental instrument or insert therefore, including a vibrating tip for contacting tooth surfaces. The tip includes a conduit or passageway for directing a fluid onto the dental or tip surfaces. The position of the fluid conduit allows the tool to include a working portion having a diameter of about 0.014 inches or less.

BACKGROUND

Many useful dental instruments employ substantial vibratory motion at a tool tip of the instrument for cleaning, scaling and like operations. The tool tips are designed to produce flexural and longitudinal vibrations with flexural motions of from about 0.02 to 0.2 mm. The tip is typically attached to an electro-mechanical part or section that can be induced to vibrate at high frequency. The instrument is driven by an electronic generator at relatively high frequencies, typically on the order of above 20 kHz, to obtain adequate motion and to minimize objectionable noise since the human hearing threshold is about 18 kHz. The energy generator and related electro-mechanical section may be any one of several types such as electro-dynamic, piezo electric, or magnetostrictive. Design of the tip and its related electro-mechanical components involves combining a number of parameters to produce mechanical resonances (harmonic vibrations) at the driving frequency to produce amplified mechanical motion, particularly at the distal tip end.

In many operations employing a vibrating tip tool, it is useful and often necessary to have a source of water or other fluid impinging upon the workpiece surfaces and/or tool surfaces in order to cool them or remove debris generated by the work. For example, in dental applications, when an ultrasonically vibrated tip contacts a tooth surface, as required for performing a cleaning operation, the moving tip against the tooth surface produces heat. The patient may experience a pain sensation which can be severe if the operator applies even mild pressure against the tooth while cleaning. Water or some other fluid is usually supplied to the tooth surface in order to remove the heat and minimize pain and possible heat damage to the tooth. In addition, a number of the electro-mechanical devices utilized in providing a vibrating tip generate heat internally during operation.

An example of an ultrasonic dental tool, wherein a handpiece containing a coil applies an electro-magnetic field to a magnetostrictive insert body to which a tool tip is fixed is described by Perdreaux in U.S. Pat. No. Re. 30,536 (CAVITRON®). In the Perdreaux design, heat caused by electrical and mechanical friction losses within the tool during vibration are dissipated by means of a cooling fluid that flows axially with respect to the tool insert, over the active magnetostrictive element or stack, emerging from an annular space between the insert and the handpiece and being directed toward the working end of the tool. The CAVITRON® arrangement is such that heat generated by the insert body warms the fluid which is then directed, as a convenient source of irrigating, flushing and/or cooling fluid, onto the active tip or workpiece area. The warm fluid minimizes reactions by patients who have sensitivity to cold temperatures.

In a number of dental operations, the vibrating tip is guided over and about tooth surfaces by the operator. The tip must be capable of penetrating between teeth and under or below the gingiva or gum line. Generally, the tip must be small in cross-section, ideally having a pointed tip with a tapered cross-section extending about 2.5 to 5 mm back from the distal tip end to allow adequate access between teeth and gingiva.

In addition, the tip is universally curved or shaped to conform to or be compatible with tooth surfaces. Useful tips will curve sufficiently to permit spanning the tooth frontal surface when entrance to abutting surfaces is needed or when access to subgingival zones about the oral cavity are required.

Experience in using such ultrasonically activated and irrigated tips has demonstrated that a combination of tip shape and fluid delivery system must be selected such that the tip is strong enough to support vibrating motion stresses at useable amplitudes. The forming process must be such that minute fractures or other weak points are not introduced into the tip material that might become focal points of breakage during use.

A number of vibrating tools, generally similar to the Perdreaux tool, as described above, are now in dental, medical, veterinary and other uses. These tools employ various designs for directing water or another fluid adjacent to or onto the surfaces being worked upon, as a means of cooling workpiece surfaces and removing debris from the work area. (The term "water" may be used interchangeably in this disclosure herein with "fluid" without intending to imply a limitation by selecting one or the other.) For example, a number of ultrasonically activated tools employ separate fluid conduits, external to the instrument itself, for conducting water and other fluids adjacent the tip or onto the workpiece or tip. Kleesattel et al in U.S. Pat. No. 3,076,904 employ a capillary, run externally to the handpiece, with a nozzle formed of a bendable metal extending very near the tip for directing water onto the dental surfaces being worked upon. A difficulty with such arrangements is that the capillary may obstruct free use of the tool tip.

A number of ultrasonic tool tips include internal fluid passageways bored along the longitudinal center axis of the tip component or body. In many such tips, a fluid discharge orifice is formed at the distal end of the tool, for directing fluid onto the workpiece. Such tip design is described, for example, by Balamuth et al in U.S. Pat. No. 3,924,335 for a piezo electric crystal vibrated dental tool. A difficulty in employing this tip design is that the tip must generally be of a relatively large diameter, on the order of greater than 1 mm, in order to have a sufficiently strong tip and a passageway that provides an adequate flow of fluid. Such a tip may be too blunt for many dental uses as it does not allow adequate tapering such that the tool thus cannot penetrate small inter-tooth spaces and can damage gums when used subgingivally.

Many tips having internal central axial passageways that include a fluid discharge orifice formed by removing a longitudinal lateral portion of the cylindrical wall of the tip as the distal tip end is approached, as shown in Haydu U.S.

Pat. No. 3,488,851 and Richman U.S. Pat. No. 3,589,012, for example. In Banko U.S. Pat. No. 3,930,173, Robinson U.S. Pat. No. 3,703,037 and Warrin U.S. Pat. No. 5,125,837, the tip is cut away such that remaining lateral walls of the distal tip from a channel for helping direct water discharging from the center axis bore onto the workpiece. A transducer activated tool tip having a water channel is shown in U.S. Pat. No. 5,567,153, which is hereby incorporated by reference for such disclosure.

All of the tips that discharge fluid from the distal end of the tip or close thereto are discharging from a tip at or before a point of high flexural motion, which motion often causes the fluid at this point to spray or form a mist adjacent to the tip and workpiece. Such spraying and misting may prevent fluid from reaching the workpiece area and, instead, dispense it over a relatively wide area, including onto the patient and operator.

Conventional dental ultrasonic scaling procedures often involve placement of an ultrasonic scaler tip into a small area such as a periodontal pocket. It is desired to make the working end of the tool such as the tip of the tool as thin as possible so that the user can observe the target area. (By tip it is understood to mean any portion of the working surface of tool itself, and may include single or monolithic structures or various connected parts that may even be removable, all of which are within the scope of the present disclosure.) However, reducing the outside diameter of the tool without reducing the diameter of a fluid passage therein, results in a thinner tip wall and an increased possibility of tool breakage during use. Ultrasonic tools such as dental scaling tools having a working end often are fabricated by starting with an unbent blank. In some cases, a back bend is put into one end of the blank (see for example, U.S. Pat. No. 6,494,714 which is hereby incorporated by reference for such disclosure) and the fluid hole is added to the blank by some means such as drilling, electro-discharge machining (EDM) or other conventional technique.

For example, in the FSI-SLI-10S dental scaler tip available from DENTSPLY International of York, Pa., the fluid hole diameter is 0.014 inches and axially transverses the majority of the working end or tip end length of the tool. After the hole is placed into the bent blank, the blank is bent into its final shape. While this device provides for an excellent and effective dental tool, when the fluid hole is bent during the final shaping of the tool, the once-circular (or other shaped) hole is deformed, such as to a more oval shape. The deformed hole has a higher probability of capturing particles inherent in the water supply system that normally passes through the fluid hole, leading to an increased possibility of becoming clogged. The dental tool described herein overcomes the deficiencies of the prior art.

SUMMARY

Described herein is a transducer activated tool for contacting workpiece surfaces and directing a fluid adjacent or onto said surfaces, comprising an activated tip having distal surfaces shaped to contact the workpiece surfaces. The tip additionally includes a fluid passageway or channel that is substantially located away from the bent regions of the tool. By locating the fluid passageway substantially away from the bent region of the tool, the fluid passageway is not subject to tool bending-induced deformations. In addition, because the portions of the tool at the end opposite the fluid passageway do not contain the internal passageway, or only some portion thereof, it is possible to make those ends of the inventive tool thinner than if they contained an internal passageway, and as low as for example, from about 0.008 to about 0.014 inches, such as from about 0.009 to about 0.014 or from about 0.01 to about 0.013 inches or about 0.0115 inches. The end of the tool without the passageway or without the majority of the passageway, and hence being capable of being made so thin, may be interchangeably termed the working end, the distal end, the tool tip or the like, all of which are intended to simply mean portions of the tool positioned at least partially away from the fluid passageway and downstream therefrom, and which portions again may be monolithic or of a single piece of material, or may be several joined or even removable pieces. Also described herein are methods of making the transducer activated tool.

DETAILED DESCRIPTION

Figure 1:
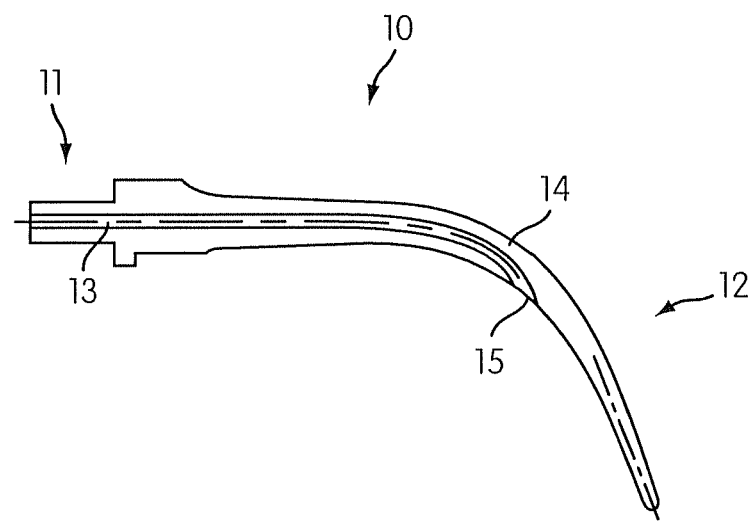
FIG. 1 is a side elevational and sectional view of a conventional prior art, ultrasonically activated dental tool having an internal fluid passageway that is positioned so that the fluid passageway discharges in a bent area of the tool.

FIG. 1 shows a conventional dental tool, designated by the number 10. Tool 10 is of the type, for illustrative purpose only, that is fitted with a magnetostrictive stack (not shown) to be inserted into dental handpiece having a transducer (also not shown) all of which are conventional in the art. The prior art tool of FIG. 1 has a connecting end generally designated by the number 11 and a working end generally designated by the number 12, which has a diameter of about 0.022 inches. Tool 10 also has an internal fluid passageway 13 and a bend such as at the area designated bend area 14. Water passageway 13 has a discharge opening or hole 15, which opening 15 and a substantial portion of fluid passageway 13 itself, is positioned within the bend area 14. This leads to the above mentioned deficiencies.

The dental tool described herein is generally designated by the number 20 on the attached drawings. Again for illustrative purposes, tool 20 is shown as being an ultrasonic dental tool, although any tool with appropriate shapes or designs useful for its intended use is within the scope of the present invention. As with conventional tool 10, tool 20 includes a connecting end generally designated by the number 21 and a working end generally designated by the number 22. Tool 20 connects to a connecting body 1 via the connecting end, which in turn connects to a magnetostrictive element 2. As one of ordinary skill in the art understands, in embodiments, tool 20 as described herein may be formed separately from or integral to the connecting body alone, or both the connecting body and magnetostrictive element.

Figure 2:
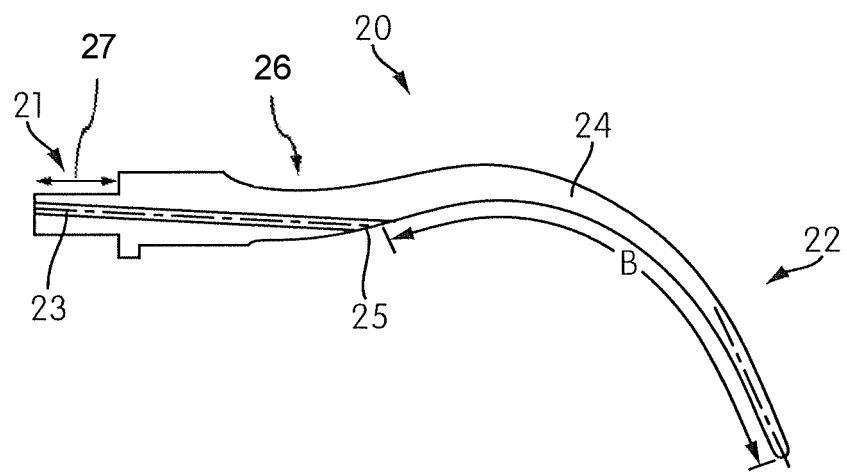
FIG. 2 is a side elevational and sectional view of an ultrasonically activated dental tool having an internal fluid passageway that is positioned so that the fluid passageway discharges at a location substantially away or removed from the bent areas of the tool.
Figure 2A:
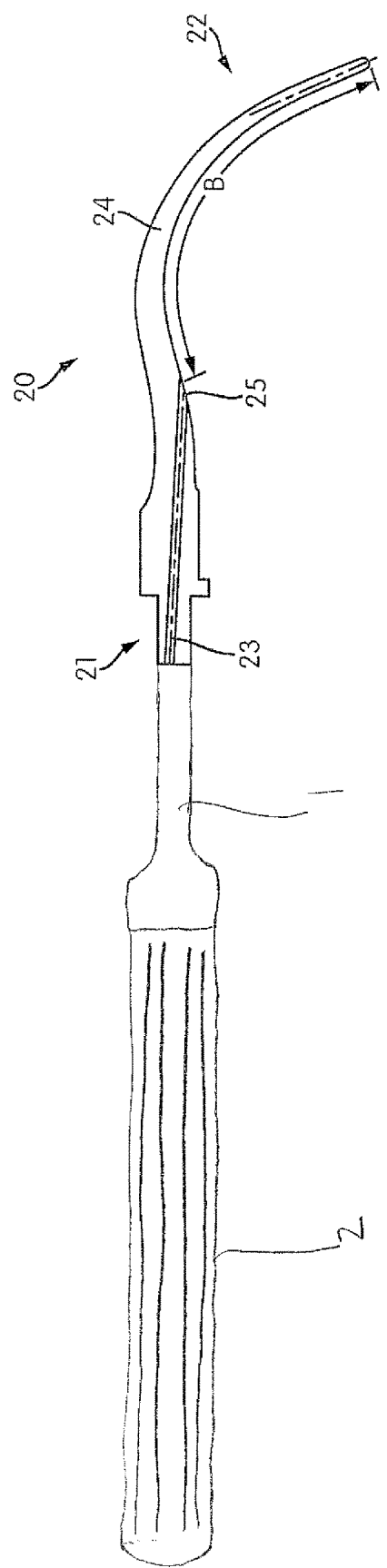
FIG. 2A is a side elevational and sectional view of an ultrasonically activated dental insert.
Figure 3:
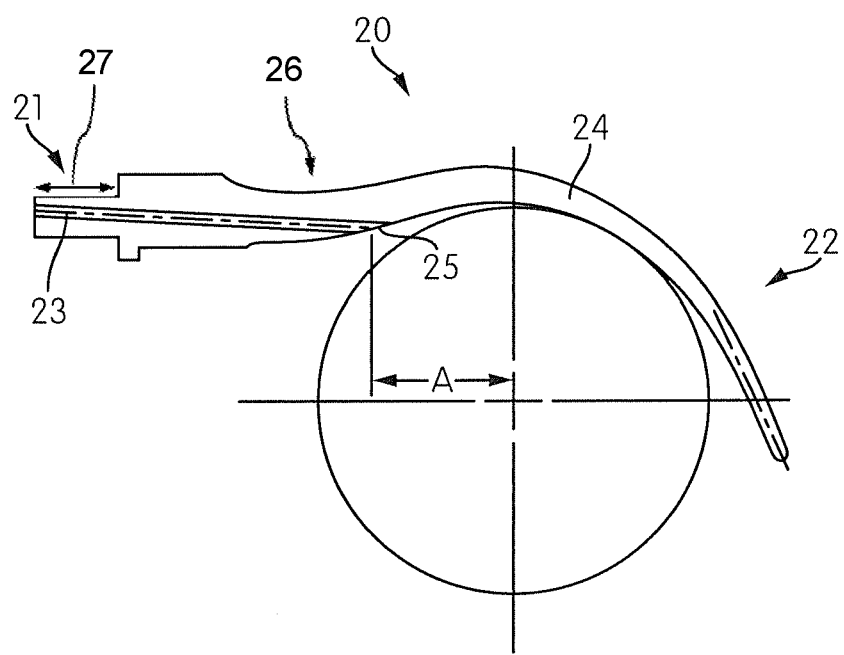
FIG. 3 is a side elevational and sectional view of an ultrasonically activated dental tool disclosed herein demonstrating the length between the discharge opening and the arc of the bend in the dental tool.

Dental tool 20 also has an internal fluid passageway 23 and a bend such as at the area designated bend area 24. Water passageway 23 has a discharge opening or hole 25, which opening 25 is positioned substantially away from bend area 24, such that the discharge opening 25 and upstream portions of passageway 23 will remain unaffected, substantially unaffected or even selectively affected by deformation thereof induced by or due to the bending procedures employed to make the other portions of the tool 20, such as those involved in fabricating the bend area 24. Referring to FIGS. 2 and 3, the dental tool 20 may include an initial curvature 26 between the connecting end 21 and the bend of the bend area 24, wherein the initial curvature 26 bends in a direction opposite to the bend of the bend area 24. In one embodiment, the discharge opening 25 is located between the initial curvature 26 and the bend of the bend area 24. The internal fluid passageway 23 may be oriented along a length 27 of the connecting end 21 at an oblique angle relative to the length 27 of the connecting end 21.

In embodiments, as shown in FIG. 3, the length A between the discharge opening 25 of the arc of the bend area 24 in the dental tool is from about 0.15 to about 0.18 inches, such as from about 0.16 to about 0.17 inches or about 0.165 inches. Or as shown in FIG. 2, the length along the tool 20 from the discharge opening 25 to the tip of the working end 22, that is, the arc length B, is from about 0.6 to about 0.8 inches such as from about 0.65 to about 0.75 inches or about 0.7 inches. In contrast, the similar length in the conventional tool, that is, the length along the tool from the discharge opening 15 to the tip of the working end 12 or its arc length is about 0.34 inches. Thus, due to the discharge opening 25 being set further away from the tip of the working end 22, the working end and the tip of the working end of the dental tool 20 described herein have a significantly smaller diameter than the working end and the tip of the working end of a conventional dental tool 10.

As described herein, due to the positioning of the discharge opening 25, the discharge opening has less deformity than the conventional dental tool 10 and has a thinner working end than the conventional dental tool. Because discharge opening 25 has little or no deformity, and is substantially circular, the discharge opening 25 is more likely to remain clear of any contaminants, such as bacteria, minerals, water impurities, scaling fragments, tooth fragments, and the like, and is thus likely to provide a cleaner fluid mist or spray and to provide improved misting or spraying over the life of the dental tool.

It will be understood that some portion of either discharge opening 25, passageway 23 or both may be partially or wholly contained within some bent portion of tool 20 and still be within the scope of the present disclosure. However, as is apparent from the present disclosure, the less that any such discharge opening is positioned within such bend portions, the more round or non-deformed the finished hole 25 will be. The less deformed the better, although some deformation may be acceptable within the scope of the disclosure as determined by the user or fabricator.

It will be appreciated that because portions of tool 20 such as working end 22 do not contain the internal passageway, portions of the tool 22 such as portions of working end 22 can be made thinner than conventionally known, and still be strong enough for their intended purpose. For example, a dental tool such as tool 20 can be made with the tip of the working end 22 having a diameter of from about 0.008 to about 0.014 inches, such as from about 0.009 to about 0.014 inches or from about 0.01 to about 0.013 inches or about 0.0115 inches.

In contrast to conventional dental tools 10 that have a partially hollowed out working end 12 that can be a fragile shell that cannot support adequate vibrational motion without danger of fracturing, the dental tool 20 described herein is not a shell and thus has improved strength such that there is no increased danger of the dental tool fracturing or breaking under regular use. That is, because the working end 22 of the dental tool 20 is not hollowed out, the dental tool described herein is better able to support the vibrational motion necessary in the regular use of the dental tool.

As described above, in conventional methods of forming an ultrasonic tool, a bend is put into one end of a blank (see for example, U.S. Pat. No. 6,494,714 which is hereby incorporated by reference for such disclosure) and the fluid passageway is added to the blank by some means such as drilling, electro-discharge machining (EDM) or other conventional technique. The blank is then bent in the opposite direction in order to form a working tool having the desired specifications and shape, that is, the passageway opening is found on the inside curve of the bend of the working tool.

In contrast to conventional tips, the working tool described herein is formed by first working the blank into the working tool having the desired specification and shape. That is, a working tool having the desired shape and specifications, including but not limited to its bending radii, length of bent arc, and the diameter or thickness of the tip of the working tool being from about 0.008 to about 0.014 inches, is first formed. Only once the working tool has been formed having the desired shape and specifications, are the passageway and passageway opening created. The passageway and passageway opening may be created by any known means such as drilling, EDM or any other conventional technique.

It should now be apparent that a device according to the present disclosure having an internal fluid passageway, such as a dental ultrasonic scaling tool, having the passageway and its discharge opening positioned away or substantially away from any bend area of the tool, allows for a fluid discharge orifice that is not or is substantially not adversely affected by deformations induced therein during the manufacturing steps of the tool that require bending. In addition, the areas of tool that do not or substantially do not contain the fluid passageway or its discharge hole, can be made thinner and with more or equal strength that such a device wherein those portions are contained or positioned within a bend area of the tool. The tool described has been characterized herein and exemplified on the drawings without attempting to show all configurations or embodiments thereof, it being understood that others are possible within the disclosed scope. The scope of the tool described herein shall therefore, only be limited by any attached claims.

The invention claimed is:

1. An ultrasonic dental insert, comprising:
a dental tool having a connecting end and a working end, the dental tool being arranged and disposed to connect to a connecting body via the connecting end,
the dental tool further comprises an internal fluid passageway that exits at a discharge opening that is located between the connecting end and a bend in the dental tool, the internal fluid passageway being oriented along a length of the connecting end at an oblique angle relative to the length of the connecting end,
wherein the dental tool includes an initial curvature between the connecting end and the bend, the initial curvature bending in a direction opposite to the bend, the discharge opening being located between the initial curvature and the bend,
wherein the discharge opening is substantially circular,
wherein the tip of the working end has a diameter of from about 0.008 inches to about 0.014 inches, and wherein a length along the dental tool from the discharge opening to the tip of the working end is from about 0.6 inches to about 0.8 inches, a length between the discharge opening and an arc of the bend is from about 0.15 inches to about 0.18 inches, and a length between the arc of the bend to the tip of the working end is from about 0.42 inches up to 0.65 inches.

2. The ultrasonic dental insert according to claim 1, wherein the tip of the working end has a diameter of from about 0.009 inches to about 0.014 inches.

3. The ultrasonic dental insert according to claim 2, wherein the diameter is from about 0.01 inches to about 0.013 inches.

4. The ultrasonic dental insert according to claim 3, wherein the diameter is about 0.0115 inches.

5. The ultrasonic dental insert according to claim 1, wherein the working end of the tool is completely solid.

6. The ultrasonic dental insert according to claim 1, wherein the discharge opening is not located in the bend.

7. The ultrasonic dental insert according to claim 1, wherein the length between the discharge opening and the arc of the bend is from about 0.15 inches to about 0.17 inches.

8. The ultrasonic dental insert according to claim 1, wherein the length between the discharge opening and the arc of the bend is about 0.165 inches.

9. The ultrasonic insert according to claim 1, wherein the length along the dental tool is from about 0.65 inches to about 0.75 inches.

10. The ultrasonic insert according to claim 1, wherein the length along the dental tool is about 0.7 inches.

11. A dental tool comprising:
a monolithic body having a connecting end and a working end, the connecting end having a configuration for attaching to a connecting body of an ultrasonic dental device, and the working end having a tip;
an internal fluid passageway extending through the monolithic body from the connecting end to a discharge opening between the connecting end and a bend in the dental tool, the discharge opening being substantially circular and free of deformation, the internal fluid passageway being oriented along a length of the connecting end at an oblique angle relative to the length of the connecting end,
wherein a length along the dental tool from the discharge opening to the tip of the working end is from about 0.6 inches to about 0.8 inches, a length from the discharge opening to an arc of the bend is from about 0.16 to about 0.17 inches, a length between the arc of the bend to the tip of the working end from about 0.43 inches up to 0.64 inches, and the tip of the working end has a diameter of from about 0.01 inches to about 0.013 inches, and
wherein the dental tool includes an initial curvature between the connecting end and the bend, the initial curvature bending in a direction opposite to the bend, the discharge opening being located between the initial curvature and the bend.

12. An ultrasonic dental insert, comprising:
a dental tool having a connecting end and a working end, the dental tool being arranged and disposed to connect to a connecting body via the connecting end,
the dental tool further comprising an internal fluid passageway that exits at a discharge opening that is located between the connecting end and a bend in the dental tool,
wherein the dental tool includes an initial curvature between the connecting end and the bend, the initial curvature bending in a direction opposite to the bend, the discharge opening being located between the initial curvature and the bend,
wherein the discharge opening is substantially circular,
wherein the tip of the working end has a diameter of from about 0.008 inches to about 0.014 inches, and
wherein a length along the dental tool from the discharge opening to the tip of the working end is from about 0.6 inches to about 0.8 inches.

13. The ultrasonic dental insert according to claim 12, wherein the working end of the tool is completely solid.

14. The ultrasonic dental insert according to claim 12, wherein the discharge opening is not located in the bend.

15. The ultrasonic dental insert according to claim 12, wherein a length between the discharge opening and an arc of the bend is from about 0.15 inches to about 0.18 inches.

16. The ultrasonic dental insert according to claim 12, wherein a length between an arc of the bend to the tip of the working end is from about 0.42 inches up to 0.65 inches.

* * * * *